United States Patent
Garcia Lara et al.

(10) Patent No.: US 9,233,150 B2
(45) Date of Patent: Jan. 12, 2016

(54) COMBINATION VACCINE

(75) Inventors: Jorge Garcia Lara, Sheffield (GB); Simon Foster, Hathersage (GB)

(73) Assignee: Absynth Biologics Limited, Sheffield (GB)

( * ) Notice: Subject to any disclaimer, the term of this patent is extended or adjusted under 35 U.S.C. 154(b) by 0 days.

(21) Appl. No.: 14/009,781

(22) PCT Filed: Apr. 11, 2012

(86) PCT No.: PCT/GB2012/050791
§ 371 (c)(1), (2), (4) Date: Oct. 3, 2013

(87) PCT Pub. No.: WO2012/140417
PCT Pub. Date: Oct. 18, 2012

(65) Prior Publication Data
US 2014/0044747 A1 Feb. 13, 2014

(30) Foreign Application Priority Data
Apr. 12, 2011 (GB) .................................. 1106162.9

(51) Int. Cl.
*A61K 39/09* (2006.01)
*A61K 39/085* (2006.01)
*C07K 14/31* (2006.01)
*A61K 9/00* (2006.01)
*A61K 45/06* (2006.01)
*A61K 39/00* (2006.01)

(52) U.S. Cl.
CPC .............. *A61K 39/085* (2013.01); *A61K 9/008* (2013.01); *A61K 9/0043* (2013.01); *A61K 45/06* (2013.01); *C07K 14/31* (2013.01); *A61K 2039/55566* (2013.01); *A61K 2039/70* (2013.01)

(58) Field of Classification Search
None
See application file for complete search history.

(56) References Cited

U.S. PATENT DOCUMENTS

2010/0047267 A1 2/2010 Masignani et al.

FOREIGN PATENT DOCUMENTS

| EP | 870829 A2 | * | 10/1998 |
| WO | WO 02077183 A2 | * | 10/2002 |
| WO | WO 02009486 A2 | * | 11/2002 |
| WO | 2005105845 A2 | | 11/2005 |

OTHER PUBLICATIONS

Mikayama et al. (Nov. 1993. Proc.Natl.Acad.Sci. USA, vol. 90 : 10056-10060).*
Rudinger et al. (Jun. 1976. Peptide Hormones. Biol.Council. pp. 5-7).*
Greenspan et al (Nature Biotechnology 7: 936-937, 1999).*
Chothia et al (The EMBO Journal, 1986, 5/4:823-26).*
Garcia-Lara, Jorge et al., "Anti-*Staphylococcus aureus* immunotherapy: current status and prospects," ScienceDirect, www.sciencedirect.com; Current Opinion in Pharmacology, vol. 9, pp. 552-557 (2009).
Gaudreau, Marie-Claude et al., "Protective immune response to a multi-gene DNA vaccine against *Staphylococcus aureus*," ScienceDirect, www.sciencedirect.com; Vaccine, vol. 25, pp. 814-824 (2007).
Fernebro, Jenny "Fighting bacterial infections—Future treatment options," www.elsevier.com/locate/drug, Drug Resistance Updates, vol. 14, pp. 125-139 (2011).
Stranger-Jones, Yukiko K. et al., "Vaccine assembly from surface proteins of *Staphylococcus aureus*," PNAS, vol. 103, No. 45, pp. 16942-16947 (Nov. 2006).

* cited by examiner

*Primary Examiner* — Jennifer Graser
(74) *Attorney, Agent, or Firm* — Seed IP Law Group PLLC

(57) ABSTRACT

The disclosure relates to a composition comprising two or more immunogenic staphylococcal polypeptides and a multivalent vaccine composition comprising the immunogenic staphylococcal polypeptides.

12 Claims, No Drawings

SEQUENCE LISTING

<160> NUMBER OF SEQ ID NOS: 36

<210> SEQ ID NO 1
<211> LENGTH: 1455
<212> TYPE: DNA
<213> ORGANISM: Staphylococcus aureus

<400> SEQUENCE: 1

| | | | | | |
|---|---|---|---|---|---|
| atggaagata | ataaaatgaa | ccgtagtctt | aactcaagac | acatttccat | gattgctata | 60 |
| ggtggtgcaa | ttgggactgg | tctatttgta | gctactggta | atatcatttc | tcaagctggt | 120 |
| cctggaggcg | ctatactcgc | ttatcttgtt | attggtgtca | tgctatattt | cttaatgtca | 180 |
| tcaattggag | agttggcaac | attttatcca | gtatcaggtt | cattcagctc | ttattcaaca | 240 |
| cgctttattg | actcatctct | tggctttacc | atgggatggt | tgtattgggc | attgtggtca | 300 |
| ttagttacaa | gtgttgatgt | catagtagcg | tcaaatgtgc | tttatttctg | ggacacattt | 360 |
| aaattttttcc | accccattac | ttggagctta | atctttatta | caattttact | attattaaac | 420 |
| attttttctg | taaaatcatt | tggagaaact | gagttttggt | tatcattgat | taaagtgtta | 480 |
| acaattatcg | tattcgttat | ttttggcttt | taatgattt | tcggtatctt | aggtggtcat | 540 |
| acatatggat | ttgaaaacta | tacaaaaggc | caagcaccgt | tgttggtgg | tatctctggt | 600 |
| ttcttaggcg | tattattagt | cgccggattt | tcggttggtg | gtacagaagt | agtagcagta | 660 |
| actgctggtg | aatcagatga | ccctaaaaag | tctatgccta | aggcaattaa | acaagtattt | 720 |
| tggcgtattc | ttttattcta | tgtcttatca | attgcagtaa | ttggtgcaat | tattccgtac | 780 |
| acagatccat | cattattaag | agcaagtagt | tcaataagtc | aaagcccatt | tacaattgta | 840 |
| ttcgatagag | taggcatagc | ctttgcagca | tcagtaatca | acgcggttat | tttaacttca | 900 |
| ttattatccg | ctgcaaattc | aggtgtttat | acaacaggca | gaatgttgta | ttccttaagt | 960 |
| tcagacaaaa | aagcaccccca | atttttaagt | aaattaaaca | agacaactaa | gttacccttta | 1020 |
| agagcattat | taactactta | tgcagtcgtt | gttattgtta | ttatttatgc | aaactttaat | 1080 |
| tcaaatgccg | ttttaatttt | acttgaaatt | attggttcaa | tgattatagt | tgtttgggga | 1140 |
| tcaagcatt | ggtcacaaat | acgattgcga | caagctatta | aaaaacaagg | tcaagaccct | 1200 |
| aataaggtcc | taccatataa | agcacccttt | tatccattag | gaccaatcat | tgtcatcact | 1260 |
| acactattat | tcttgctatt | tggtggctca | gttgaatata | ttttaaaaga | tcaatggtta | 1320 |
| aatgcttttta | aaaacttttt | acctttaatc | attctagcgt | tgatttactt | tattcataaa | 1380 |
| atcattcaca | aaacaaaatt | tgtaaagcta | gaaacaatta | atttaaaacc | acacgattat | 1440 |
| gacaatcaaa | aataa | | | | | 1455 |

<210> SEQ ID NO 2
<211> LENGTH: 1026
<212> TYPE: DNA
<213> ORGANISM: Staphylococcus aureus

<400> SEQUENCE: 2

| | | | | | |
|---|---|---|---|---|---|
| atgactaaag | atatattaat | actagctgtt | gaaacaagtt | gtgatgaaac | aagcgttagt | 60 |
| gttataaaaa | atggcagaga | tattttatca | aatacagttt | taagtcagat | tgaaagtcat | 120 |
| aaacgatttg | gcggtgtcgt | tcccgaagtg | gcaagtagac | atcacgttga | aggtataaca | 180 |
| gcaacaataa | acgaggctct | aggggatgcc | gatgtatcaa | tagaagatat | tgatgccata | 240 |
| gcggttacag | aaggccctgg | actaattggt | gcgttactaa | taggtgttaa | tgcagccaaa | 300 |
| gcattggcat | ttgcttacga | taagccactt | attcctgttc | atcatattgc | aggacatata | 360 |

-continued

| | |
|---|---|
| tatgctaatc acatagaaga gccattaaca ttcccgctaa ttgcacttat tgtttcaggt | 420 |
| ggacatactg aattagttta tatgaaggat catttatcat ttgaagtcat tggtgaaaca | 480 |
| cgagatgacg cagtaggtga ggcttatgat aaagtggcac gaacaattgg tttaaattat | 540 |
| ccaggtggtc cacaagttga tcggttggct gctgaaggtg aagatactta ttcattccct | 600 |
| cgtgtttggt tggataaaga tagttatgat tttagttta gtgggttgaa aagtgccgta | 660 |
| atcaatcaac ttcacaatca acgacaaaaa aatattccaa tcattgaagc taacgtagca | 720 |
| acgagctttc aaaacagtgt tgtagaggtg ctcacgttta aagctattca agcttgtaaa | 780 |
| gaatatggtg ttcagcgatt aattgttgct ggtggcgtgg cgagtaataa aggattacgt | 840 |
| caatctttag cggatcaatg caaagtcaat gacattcaat taactatccc aagtcctaaa | 900 |
| ttatgcacag ataatgctgc aatgataggc gttgccggcc actatttgta tcagcaaggt | 960 |
| cgatttgctg atttagcatt aaatgggcac agcaatatag atttagaaga gtattctgca | 1020 |
| gaataa | 1026 |

<210> SEQ ID NO 3
<211> LENGTH: 1320
<212> TYPE: DNA
<213> ORGANISM: Staphylococcus aureus

<400> SEQUENCE: 3

| | |
|---|---|
| atggatgata aaacgaagaa cgatcaacaa gaatcaaatg aagataaaga tgaattagaa | 60 |
| ttatttacga ggaatacatc taagaaaaga cggcaaagaa aaagatcaaa ggctacacat | 120 |
| ttttctaatc aaaataaaga tgatacatct caacaagctg attttgatga agaaatttac | 180 |
| ttgataaata aagacttcaa aaaagaagaa agcaatgata aaaataatga ttctgcttct | 240 |
| agtcatgcga atgataataa tatcgatgat tctacagact ctaatattga aaatgaggat | 300 |
| tatagatata atcaagaaat tgacgaccaa atgaatcga atgtaatttc agtcgacaac | 360 |
| gaacaacctc aatcagctcc taagaacaa aatagcgact cgattgatga ggaaacagta | 420 |
| acgaaaaaag aacgaaaaag taaagtaaca caattaaagc cattaacact tgaagaaaag | 480 |
| cggaagttaa gacgtaagcg acaaaagcga atccaataca gtgttattac aatattggta | 540 |
| ttgttgattg ctgttatatt aatttacatg ttttcaccac ttagtaaaat tgcgcatgta | 600 |
| aatataaatg gaaataatca cgttagtact tcaaagataa acaaagtttt aggtgttaaa | 660 |
| aatgattcaa ggatgtatac gtttagtaaa aaaaatgcta ttaatgatct cgaagagaat | 720 |
| ccattaatca aaagtgttga gatacacaag caattaccaa acacattaaa cgtagatatc | 780 |
| acagaaaatg aaattattgc tttagtgaaa tataaaggta atatttacc tttattagaa | 840 |
| aatggtaaat tgcttaaagg ttcaaatgat gtcaaaatta atgatgcacc tgtcatggat | 900 |
| ggtttcaaag gtacaaaaga agatgatatg attaaggcgt tatctgaaat gacacctgaa | 960 |
| gttagacgat atattgccga agtgacatac gccccaagta aaaacaaaca aagcagaatt | 1020 |
| gaattgttta cgacagatgg acttcaagta atcggtgata tttcgacgat atctaagaaa | 1080 |
| atgaaatatt atccgcagat gtcacaatca ttatcaaggg atagttcggg taaactaaaa | 1140 |
| acacgaggct atattgattt atcagtcggt gcttcattta tcccataccg tggaaacacg | 1200 |
| tctagtcaat cagaaagcga taaaaatgtg actaaatcat ctcaagagga aaatcaagca | 1260 |
| aaagaagaat tacaaagcgt tttaaacaaa attaacaaac aatcaagtaa gaataattaa | 1320 |

<210> SEQ ID NO 4

```
<211> LENGTH: 393
<212> TYPE: DNA
<213> ORGANISM: Staphylococcus aureus

<400> SEQUENCE: 4
atgaaaaata aagtagaaca tatagaaaat cagtacacgt cgcaagagaa caagaaaaaa        60
caacgtcaaa aaatgaaaat gcgtgttgtt cgtaggcgta ttacagtatt tgcgggcgta       120
ttacttgcga taattgttgt tttatcaatc ttgcttgttg tccaaaaaca tcgcaatgat       180
attgatgcac aggagcgaaa agcgaaagaa gcacagtttc aaaagcaaca aaatgaagaa       240
attgcgttaa agaaaagtt gaataatctg aatgacaaag attacattga aaaaattgcg        300
cgtgatgatt attacttaag caacaaaggt gaagtgattt ttaggttgcc agaagacaaa       360
gattcgtcta gctcaaaatc ttcgaaaaaa taa                                    393

<210> SEQ ID NO 5
<211> LENGTH: 402
<212> TYPE: DNA
<213> ORGANISM: Staphylococcus aureus

<400> SEQUENCE: 5
atggctgtag aaaagtgta ccaaccatat gacgaacaag tttataatag tataccgaag         60
caacaaccac aaactaagcc cgaaagaag actgtttcga aaaagtggt tgtacaatta        120 actaaatttg aaaagttttt atacataact ttgattactg taattgctat gttaagtatt       180
tatatgctat ctttaaaaat ggatgcgtat gatacgcgag aaagattgc agatttagat        240 tataaaatag ataacaatc aagtgaaaac agtgctttac aatctgaaat caaaagaat        300 tcttcttatg aacgcatata cgaaaaggct aagaaacagg ggatgagcct tgagaacgat       360
aatgtaaagg tagtgcgtag taatggcgaa gcaaaaaatt aa                         402

<210> SEQ ID NO 6
<211> LENGTH: 42
<212> TYPE: DNA
<213> ORGANISM: Artificial Sequence
<220> FEATURE:
<223> OTHER INFORMATION: selected pheP peptide DNA sequence

<400> SEQUENCE: 6
ctttatttct gggacacatt taaattttc caccccatta ct                            42

<210> SEQ ID NO 7
<211> LENGTH: 687
<212> TYPE: DNA
<213> ORGANISM: Artificial Sequence
<220> FEATURE:
<223> OTHER INFORMATION: extramembranous ydiE/gcp sequence

<400> SEQUENCE: 7
gttcatcata ttgcaggaca tatatatgct aatcacatag aagagccatt aacattcccg        60
ctaattgcac ttattgtttc aggtggacat actgaattag tttatatgaa ggatcattta       120
tcatttgaag tcattggtga aacacgagat gacgcagtag gtgaggctta tgataaagtg       180
gcacgaacaa ttggtttaaa ttatccaggt ggtccacaag ttgatcggtt ggctgctgaa       240
ggtgaagata cttattcatt ccctcgtgtt tggttggata agatagtta tgattttagt       300 tttagtgggt tgaaaagtgc cgtaatcaat caacttcaca atcaacgaca aaaaaatatt       360
ccaatcattg aagctaacgt agcaacgagc tttcaaaaca gtgttgtaga ggtgctcacg       420
tttaaagcta ttcaagcttg taaagaatat ggtgttcagc gattaattgt tgctggtggc       480
```

```
gtggcgagta ataaaggatt acgtcaatct ttagcggatc aatgcaaagt caatgacatt      540
caattaacta tcccaagtcc taaattatgc acagataatg ctgcaatgat aggcgttgcc      600
ggccactatt tgtatcagca aggtcgattt gctgatttag cattaaatgg gcacagcaat      660
atagatttag aagagtattc tgcagaa                                          687

<210> SEQ ID NO 8
<211> LENGTH: 741
<212> TYPE: DNA
<213> ORGANISM: Artificial Sequence
<220> FEATURE:
<223> OTHER INFORMATION: extramembranous divIB sequence, also named in
      preceding patent DivIB-1

<400> SEQUENCE: 8
ccacttagta aaattgcgca tgtaaatata atggaaata atcacgttag tacttcaaag       60
ataaacaaag ttttaggtgt taaaaatgat tcgaggatgt atacgtttag taaaaaaaat      120
gctattaatg atctcgaaga ggatccatta atcaaaagtg ttgagataca caagcaatta     180
ccaaacacat taaacgtaga tatcacagaa aatgaaatta ttgctttagt gaaatataaa     240
ggtaaatatt taccttttatt agaaaatggt aaattgctta aaggttcaaa tgatgtcaaa    300
attaatgatg cacctgtcat ggatggtttc aaaggtacaa agaagatga tatgattaag      360 gcgttatctg aaatgacacc tgaagttaga cgatatattg ccgaagtgac atacgcccca    420
agtaaaaaca aacaaagcag aattgaattg tttacgacag atggacttca agtaatcggt    480
gatatttcga cgtatatcta aaaatgaaa tattatccgc agatgtcaca atcattatca    540
agggatagtt cgggtaaact aaaaacaaga ggctatattg atttatcagt cggtgcttca     600
tttatcccat accgtggaaa cacgtctagt caatcagaaa gcgataaaaa tgtgactaaa     660
tcatctcaag aggaaaatca agcaaagaa gaattacaaa gcgttttaaa caaaattaac    720
aaacaatcaa gtaagaataa t                                               741

<210> SEQ ID NO 9
<211> LENGTH: 225
<212> TYPE: DNA
<213> ORGANISM: Artificial Sequence
<220> FEATURE:
<223> OTHER INFORMATION: extramembranous divIC sequence

<400> SEQUENCE: 9
aaacatcgca atgatattga tgcacaggag cgaaaagcga agaagcaca gtttcaaaag       60 caacaaaatg aagaaattgc gttaaaagaa aagttgaata atctgaatga caagagattac    120 attgaaaaaa ttgcgcgtga tgattattac ttaagcaaca aaggtgaagt gattttttag     180
ttgccagaag acaaagattc gtctagctca aaatcttcga aaaaa                     225

<210> SEQ ID NO 10
<211> LENGTH: 204
<212> TYPE: DNA
<213> ORGANISM: Artificial Sequence
<220> FEATURE:
<223> OTHER INFORMATION: extramembranous ftsL sequence

<400> SEQUENCE: 10
aaaatggatg cgtatgatac gcgaggaaag attgcagatt tagattataa aatagataaa      60
caatcaagtg aaaacagtgc tttacaatct gaaatcaaaa agaattcttc ttatgaacgc     120
atatacgaaa aggctaagaa acaggggatg agccttgaga acgataatgt aaaggtagtg     180
```

```
cgtagtaatg gcgaagcaaa aaat                                         204

<210> SEQ ID NO 11
<211> LENGTH: 720
<212> TYPE: DNA
<213> ORGANISM: Artificial Sequence
<220> FEATURE:
<223> OTHER INFORMATION: (T7-tag / intermediate bases / ydiE
      extramembranous / intermediate bases / His-tag sequence

<400> SEQUENCE: 11
atggctgttc atcatattgc aggacatata tatgctaatc acatagaaga gccattaaca      60
ttcccgctaa ttgcacttat tgtttcaggt ggacatactg aattagttta tatgaaggat     120
catttatcat ttgaagtcat tggtgaaaca cgagatgacg cagtaggtga ggcttatgat     180
aaagtggcac gaacaattgg tttaaattat ccaggtggtc cacaagttga tcggttggct     240
gctgaaggtg aagatactta ttcattccct cgtgtttggt tggataaaga tagttatgat     300
tttagtttta gtgggttgaa aagtgccgta atcaatcaac ttcacaatca acgacaaaaa     360
aatattccaa tcattgaagc taacgtagca acgagctttc aaaacagtgt tgtagaggtg     420 ctcacgtttaa aagctattca agcttgtaaa gaatatggtg ttcagcgatt aattgttgct     480
ggtggcgtgg cgagtaataa aggattacgt caatctttag cggatcaatg caaagtcaat     540
gacattcaat taactatccc aagtcctaaa ttatgcacag ataatgctgc aatgataggc     600
gttgccggcc actatttgta tcagcaaggt cgatttgctg atttagcatt aaatgggcac     660
agcaatatag atttagaaga gtattctgca gaactcgagc accaccacca ccaccactga     720

<210> SEQ ID NO 12
<211> LENGTH: 774
<212> TYPE: DNA
<213> ORGANISM: Artificial Sequence
<220> FEATURE:
<223> OTHER INFORMATION: T7-tag / intermediate bases / divIB
      extramembranous / intermediate bases / His-tag sequence

<400> SEQUENCE: 12
atggctccac ttagtaaaat tgcgcatgta aatataaatg gaataatcca cgttagtact      60
tcaaagataa acaaagtttt aggtgttaaa aatgattcga ggatgtatac gtttagtaaa     120
aaaaatgcta ttaatgatct cgaagaggat ccattaatca aaagtgttga gatacacaag     180
caattaccaa acacattaaa cgtagatatc acagaaaatg aaattattgc tttagtgaaa     240
tataaaggta aatatttacc tttattagaa aatggtaaat tgcttaaagg ttcaaatgat     300
gtcaaaatta atgatgcacc tgtcatggat ggtttcaaag gtacaaaaga agatgatatg     360
attaaggcgt tatctgaaat gacacctgaa gttagacgat atattgccga agtgacatac     420
gccccaagta aaacaaaca aagcagaatt gaattgttta cgacagatgg acttcaagta     480
atcggtgata tttcgacgat atctaagaaa atgaaatatt tccgcagat gtcacaatca     540 ttatcaaggg atagttcggg taaactaaaa acaagaggct atattgattt atcagtcggt     600
gcttcattta tcccataccg tggaaacacg tctagtcaat cagaaagcga taaaaatgtg     660
actaaatcat ctcaagagga aaatcaagca aagaagaat tacaaagcgt tttaaacaaa     720
attaacaaac aatcaagtaa gaataatctc gagcaccacc accaccacca ctga           774

<210> SEQ ID NO 13
<211> LENGTH: 255
<212> TYPE: DNA
```

```
<213> ORGANISM: Artificial Sequence
<220> FEATURE:
<223> OTHER INFORMATION: T7-tag / intermediate bases /
      divIC extramembranous / intermediate bases / His-tag sequence

<400> SEQUENCE: 13
atggctaaac atcgcaatga tattgatgca caggagcgaa aagcgaaaga agcacagttt    60
caaaagcaac aaaatgaaga aattgcgtta aagaaaagt tgaataatct gaatgacaaa   120
gattacattg aaaaaattgc gcgtgatgat tattacttaa gcaacaaagg tgaagtgatt   180
tttaggttgc agaagacaa agattcgtct agctcaaaat cttcgaaaaa actcgagcac   240
caccaccacc accac                                                   255

<210> SEQ ID NO 14
<211> LENGTH: 234
<212> TYPE: DNA
<213> ORGANISM: Artificial Sequence
<220> FEATURE:
<223> OTHER INFORMATION: T7-tag / intermediate bases / ftsL
      extramembranous / intermediate bases / His-tag sequence

<400> SEQUENCE: 14
atggctaaaa tggatgcgta tgatacgcga ggaaagattg cagatttaga ttataaaata    60
gataaacaat caagtgaaaa cagtgctta caatctgaaa tcaaaagaa ttcttcttat    120 gaacgcatat acgaaaaggc taagaaacag gggatgagcc ttgagaacga taatgtaaag   180
gtagtgcgta gtaatggcga agcaaaaaat ctcgagcacc accaccacca ccac        234

<210> SEQ ID NO 15
<211> LENGTH: 484
<212> TYPE: PRT
<213> ORGANISM: Staphylococcus aureus

<400> SEQUENCE: 15

Met Glu Asp Asn Lys Met Asn Arg Ser Leu Asn Ser Arg His Ile Ser
1               5                   10                  15

Met Ile Ala Ile Gly Gly Ala Ile Gly Thr Gly Leu Phe Val Ala Thr
            20                  25                  30

Gly Asn Ile Ile Ser Gln Ala Gly Pro Gly Gly Ala Ile Leu Ala Tyr
        35                  40                  45

Leu Val Ile Gly Val Met Leu Tyr Phe Leu Met Ser Ser Ile Gly Glu
    50                  55                  60

Leu Ala Thr Phe Tyr Pro Val Ser Gly Ser Phe Ser Ser Tyr Ser Thr
65                  70                  75                  80

Arg Phe Ile Asp Ser Ser Leu Gly Phe Thr Met Gly Trp Leu Tyr Trp
                85                  90                  95

Ala Leu Trp Ser Leu Val Thr Ser Val Asp Val Ile Val Ala Ser Asn
            100                 105                 110

Val Leu Tyr Phe Trp Asp Thr Phe Lys Phe Phe His Pro Ile Thr Trp
        115                 120                 125

Ser Leu Ile Phe Ile Thr Ile Leu Leu Leu Asn Ile Phe Ser Val
    130                 135                 140

Lys Ser Phe Gly Glu Thr Glu Phe Trp Leu Ser Leu Ile Lys Val Leu
145                 150                 155                 160

Thr Ile Ile Val Phe Val Ile Phe Gly Phe Leu Met Ile Phe Gly Ile
                165                 170                 175

Leu Gly Gly His Thr Tyr Gly Phe Glu Asn Tyr Thr Lys Gly Gln Ala
            180                 185                 190
```

```
Pro Phe Val Gly Gly Ile Ser Gly Phe Leu Gly Val Leu Val Ala
        195                 200                 205

Gly Phe Ser Val Gly Gly Thr Glu Val Val Ala Val Thr Ala Gly Glu
    210                 215                 220

Ser Asp Asp Pro Lys Lys Ser Met Pro Lys Ala Ile Lys Gln Val Phe
225                 230                 235                 240

Trp Arg Ile Leu Leu Phe Tyr Val Leu Ser Ile Ala Val Ile Gly Ala
                245                 250                 255

Ile Ile Pro Tyr Thr Asp Pro Ser Leu Leu Arg Ala Ser Ser Ser Ile
            260                 265                 270

Ser Gln Ser Pro Phe Thr Ile Val Phe Asp Arg Val Gly Ile Ala Phe
        275                 280                 285

Ala Ala Ser Val Ile Asn Ala Val Ile Leu Thr Ser Leu Leu Ser Ala
    290                 295                 300

Ala Asn Ser Gly Val Tyr Thr Thr Gly Arg Met Leu Tyr Ser Leu Ser
305                 310                 315                 320

Ser Asp Lys Lys Ala Pro Gln Phe Leu Ser Lys Leu Asn Lys Thr Thr
                325                 330                 335

Lys Leu Pro Leu Arg Ala Leu Thr Thr Tyr Ala Val Val Val Ile
            340                 345                 350

Val Ile Ile Tyr Ala Asn Phe Asn Ser Asn Ala Val Phe Asn Leu Leu
        355                 360                 365

Glu Ile Ile Gly Ser Met Ile Ile Val Val Trp Gly Ser Ser Ile Trp
    370                 375                 380

Ser Gln Ile Arg Leu Arg Gln Ala Ile Lys Lys Gln Gly Gln Asp Pro
385                 390                 395                 400

Asn Lys Val Leu Pro Tyr Lys Ala Pro Phe Tyr Pro Leu Gly Pro Ile
                405                 410                 415

Ile Val Ile Thr Thr Leu Leu Phe Leu Leu Phe Gly Gly Ser Val Glu
            420                 425                 430

Tyr Ile Leu Lys Asp Gln Trp Leu Asn Ala Phe Lys Asn Phe Leu Pro
        435                 440                 445

Leu Ile Ile Leu Ala Leu Ile Tyr Phe Ile His Lys Ile Ile His Lys
    450                 455                 460

Thr Lys Phe Val Lys Leu Glu Thr Ile Asn Leu Lys Pro His Asp Tyr
465                 470                 475                 480

Asp Asn Gln Lys

<210> SEQ ID NO 16
<211> LENGTH: 341
<212> TYPE: PRT
<213> ORGANISM: Staphylococcus aureus

<400> SEQUENCE: 16

Met Thr Lys Asp Ile Leu Ile Leu Ala Val Glu Thr Ser Cys Asp Glu
1               5                   10                  15

Thr Ser Val Ser Val Ile Lys Asn Gly Arg Asp Ile Leu Ser Asn Thr
            20                  25                  30

Val Leu Ser Gln Ile Glu Ser His Lys Arg Phe Gly Gly Val Val Pro
        35                  40                  45

Glu Val Ala Ser Arg His His Val Glu Gly Ile Thr Ala Thr Ile Asn
    50                  55                  60

Glu Ala Leu Gly Asp Ala Asp Val Ser Ile Glu Asp Ile Asp Ala Ile
65                  70                  75                  80
```

```
Ala Val Thr Glu Gly Pro Gly Leu Ile Gly Ala Leu Leu Ile Gly Val
                85                  90                  95

Asn Ala Ala Lys Ala Leu Ala Phe Ala Tyr Asp Lys Pro Leu Ile Pro
            100                 105                 110

Val His His Ile Ala Gly His Ile Tyr Ala Asn His Ile Glu Glu Pro
        115                 120                 125

Leu Thr Phe Pro Leu Ile Ala Leu Ile Val Ser Gly His Thr Glu
    130                 135                 140

Leu Val Tyr Met Lys Asp His Leu Ser Phe Glu Val Ile Gly Glu Thr
145                 150                 155                 160

Arg Asp Asp Ala Val Gly Glu Ala Tyr Asp Lys Val Ala Arg Thr Ile
                165                 170                 175

Gly Leu Asn Tyr Pro Gly Gly Pro Gln Val Asp Arg Leu Ala Ala Glu
            180                 185                 190

Gly Glu Asp Thr Tyr Ser Phe Pro Arg Val Trp Leu Asp Lys Asp Ser
        195                 200                 205

Tyr Asp Phe Ser Phe Ser Gly Leu Lys Ser Ala Val Ile Asn Gln Leu
    210                 215                 220

His Asn Gln Arg Gln Lys Asn Ile Pro Ile Glu Ala Asn Val Ala
225                 230                 235                 240

Thr Ser Phe Gln Asn Ser Val Val Glu Val Leu Thr Phe Lys Ala Ile
                245                 250                 255

Gln Ala Cys Lys Glu Tyr Gly Val Gln Arg Leu Ile Val Ala Gly Gly
            260                 265                 270

Val Ala Ser Asn Lys Gly Leu Arg Gln Ser Leu Ala Asp Gln Cys Lys
        275                 280                 285

Val Asn Asp Ile Gln Leu Thr Ile Pro Ser Pro Lys Leu Cys Thr Asp
    290                 295                 300

Asn Ala Ala Met Ile Gly Val Ala Gly His Tyr Leu Tyr Gln Gln Gly
305                 310                 315                 320

Arg Phe Ala Asp Leu Ala Leu Asn Gly His Ser Asn Ile Asp Leu Glu
                325                 330                 335

Glu Tyr Ser Ala Glu
            340

<210> SEQ ID NO 17
<211> LENGTH: 439
<212> TYPE: PRT
<213> ORGANISM: Staphylococcus aureus

<400> SEQUENCE: 17

Met Asp Asp Lys Thr Lys Asn Asp Gln Gln Glu Ser Asn Glu Asp Lys
1               5                   10                  15

Asp Glu Leu Glu Leu Phe Thr Arg Asn Thr Ser Lys Lys Arg Arg Gln
            20                  25                  30

Arg Lys Arg Ser Lys Ala Thr His Phe Ser Asn Gln Asn Lys Asp Asp
        35                  40                  45

Thr Ser Gln Gln Ala Asp Phe Asp Glu Glu Ile Tyr Leu Ile Asn Lys
    50                  55                  60

Asp Phe Lys Lys Glu Ser Asn Asp Lys Asn Asn Asp Ser Ala Ser
65                  70                  75                  80

Ser His Ala Asn Asp Asn Asn Ile Asp Asp Ser Thr Asp Ser Asn Ile
                85                  90                  95

Glu Asn Glu Asp Tyr Arg Tyr Asn Gln Glu Ile Asp Asp Gln Asn Glu
```

-continued

```
                100                 105                 110
Ser Asn Val Ile Ser Val Asp Asn Glu Gln Pro Gln Ser Ala Pro Lys
        115                 120                 125

Glu Gln Asn Ser Asp Ser Ile Asp Glu Glu Thr Val Thr Lys Lys Glu
130                 135                 140

Arg Lys Ser Lys Val Thr Gln Leu Lys Pro Leu Thr Leu Glu Glu Lys
145                 150                 155                 160

Arg Lys Leu Arg Arg Lys Arg Gln Lys Arg Ile Gln Tyr Ser Val Ile
                165                 170                 175

Thr Ile Leu Val Leu Leu Ile Ala Val Ile Leu Ile Tyr Met Phe Ser
            180                 185                 190

Pro Leu Ser Lys Ile Ala His Val Asn Ile Asn Gly Asn Asn His Val
        195                 200                 205

Ser Thr Ser Lys Ile Asn Lys Val Leu Gly Val Lys Asn Asp Ser Arg
    210                 215                 220

Met Tyr Thr Phe Ser Lys Lys Asn Ala Ile Asn Asp Leu Glu Glu Asn
225                 230                 235                 240

Pro Leu Ile Lys Ser Val Glu Ile His Lys Gln Leu Pro Asn Thr Leu
                245                 250                 255

Asn Val Asp Ile Thr Glu Asn Glu Ile Ile Ala Leu Val Lys Tyr Lys
            260                 265                 270

Gly Lys Tyr Leu Pro Leu Leu Glu Asn Gly Lys Leu Leu Lys Gly Ser
        275                 280                 285

Asn Asp Val Lys Ile Asn Asp Ala Pro Val Met Asp Gly Phe Lys Gly
    290                 295                 300

Thr Lys Glu Asp Asp Met Ile Lys Ala Leu Ser Glu Met Thr Pro Glu
305                 310                 315                 320

Val Arg Arg Tyr Ile Ala Glu Val Thr Tyr Ala Pro Ser Lys Asn Lys
                325                 330                 335

Gln Ser Arg Ile Glu Leu Phe Thr Thr Asp Gly Leu Gln Val Ile Gly
            340                 345                 350

Asp Ile Ser Thr Ile Ser Lys Lys Met Lys Tyr Tyr Pro Gln Met Ser
        355                 360                 365

Gln Ser Leu Ser Arg Asp Ser Ser Gly Lys Leu Lys Thr Arg Gly Tyr
    370                 375                 380

Ile Asp Leu Ser Val Gly Ala Ser Phe Ile Pro Tyr Arg Gly Asn Thr
385                 390                 395                 400

Ser Ser Gln Ser Glu Ser Asp Lys Asn Val Thr Lys Ser Ser Gln Glu
                405                 410                 415

Glu Asn Gln Ala Lys Glu Glu Leu Gln Ser Val Leu Asn Lys Ile Asn
            420                 425                 430

Lys Gln Ser Ser Lys Asn Asn
        435

<210> SEQ ID NO 18
<211> LENGTH: 130
<212> TYPE: PRT
<213> ORGANISM: Staphylococcus aureus

<400> SEQUENCE: 18

Met Lys Asn Lys Val Glu His Ile Glu Asn Gln Tyr Thr Ser Gln Glu
1               5                   10                  15

Asn Lys Lys Lys Gln Arg Gln Lys Met Lys Met Arg Val Val Arg Arg
            20                  25                  30
```

```
Arg Ile Thr Val Phe Ala Gly Val Leu Leu Ala Ile Val Val Leu
         35                  40                  45

Ser Ile Leu Leu Val Val Gln Lys His Arg Asn Asp Ile Asp Ala Gln
 50                  55                  60

Glu Arg Lys Ala Lys Glu Ala Gln Phe Gln Lys Gln Gln Asn Glu Glu
 65                  70                  75                  80

Ile Ala Leu Lys Glu Lys Leu Asn Asn Leu Asn Asp Lys Asp Tyr Ile
                 85                  90                  95

Glu Lys Ile Ala Arg Asp Asp Tyr Tyr Leu Ser Asn Lys Gly Glu Val
                100                 105                 110

Ile Phe Arg Leu Pro Glu Asp Lys Asp Ser Ser Ser Lys Ser Ser
                115                 120                 125

Lys Lys
    130

<210> SEQ ID NO 19
<211> LENGTH: 133
<212> TYPE: PRT
<213> ORGANISM: Staphylococcus aureus

<400> SEQUENCE: 19

Met Ala Val Glu Lys Val Tyr Gln Pro Tyr Asp Glu Gln Val Tyr Asn
 1                5                  10                  15

Ser Ile Pro Lys Gln Gln Pro Thr Lys Pro Glu Lys Lys Thr Val
                 20                  25                  30

Ser Arg Lys Val Val Gln Leu Thr Lys Phe Glu Lys Val Leu Tyr
             35                  40                  45

Ile Thr Leu Ile Thr Val Ile Ala Met Leu Ser Ile Tyr Met Leu Ser
 50                  55                  60

Leu Lys Met Asp Ala Tyr Asp Thr Arg Gly Lys Ile Ala Asp Leu Asp
 65                  70                  75                  80

Tyr Lys Ile Asp Lys Gln Ser Ser Glu Asn Ser Ala Leu Gln Ser Glu
                 85                  90                  95

Ile Lys Lys Asn Ser Ser Tyr Glu Arg Ile Tyr Glu Lys Ala Lys Lys
                100                 105                 110

Gln Gly Met Ser Leu Glu Asn Asp Asn Val Lys Val Val Arg Ser Asn
                115                 120                 125

Gly Glu Ala Lys Asn
    130

<210> SEQ ID NO 20
<211> LENGTH: 14
<212> TYPE: PRT
<213> ORGANISM: Artificial Sequence
<220> FEATURE:
<223> OTHER INFORMATION: selected extramembranous PhePsequence

<400> SEQUENCE: 20

Leu Tyr Phe Trp Asp Thr Phe Lys Phe Phe His Pro Ile Thr
 1                5                  10

<210> SEQ ID NO 21
<211> LENGTH: 229
<212> TYPE: PRT
<213> ORGANISM: Artificial Sequence
<220> FEATURE:
<223> OTHER INFORMATION: extramembranous YdiE sequence

<400> SEQUENCE: 21
```

```
Val His His Ile Ala Gly His Ile Tyr Ala Asn His Ile Glu Glu Pro
1               5                   10                  15
Leu Thr Phe Pro Leu Ile Ala Leu Ile Val Ser Gly Gly His Thr Glu
                20                  25                  30
Leu Val Tyr Met Lys Asp His Leu Ser Phe Glu Val Ile Gly Glu Thr
            35                  40                  45
Arg Asp Asp Ala Val Gly Glu Ala Tyr Asp Lys Val Ala Arg Thr Ile
        50                  55                  60
Gly Leu Asn Tyr Pro Gly Pro Gln Val Asp Arg Leu Ala Ala Glu
65                  70                  75                  80
Gly Glu Asp Thr Tyr Ser Phe Pro Arg Val Trp Leu Asp Lys Asp Ser
                85                  90                  95
Tyr Asp Phe Ser Phe Ser Gly Leu Lys Ser Ala Val Ile Asn Gln Leu
            100                 105                 110
His Asn Gln Arg Gln Lys Asn Ile Pro Ile Glu Ala Asn Val Ala
        115                 120                 125
Thr Ser Phe Gln Asn Ser Val Val Glu Val Leu Thr Phe Lys Ala Ile
    130                 135                 140
Gln Ala Cys Lys Glu Tyr Gly Val Gln Arg Leu Ile Val Ala Gly Gly
145                 150                 155                 160
Val Ala Ser Asn Lys Gly Leu Arg Gln Ser Leu Ala Asp Gln Cys Lys
                165                 170                 175
Val Asn Asp Ile Gln Leu Thr Ile Pro Ser Pro Lys Leu Cys Thr Asp
            180                 185                 190
Asn Ala Ala Met Ile Gly Val Ala Gly His Tyr Leu Tyr Gln Gln Gly
        195                 200                 205
Arg Phe Ala Asp Leu Ala Leu Asn Gly His Ser Asn Ile Asp Leu Glu
    210                 215                 220
Glu Tyr Ser Ala Glu
225

<210> SEQ ID NO 22
<211> LENGTH: 247
<212> TYPE: PRT
<213> ORGANISM: Artificial Sequence
<220> FEATURE:
<223> OTHER INFORMATION: extramembranous DivIB sequence, also named in
      preceding patent DivIB-1

<400> SEQUENCE: 22

Pro Leu Ser Lys Ile Ala His Val Asn Ile Asn Gly Asn Asn His Val
1               5                   10                  15
Ser Thr Ser Lys Ile Asn Lys Val Leu Gly Val Lys Asn Asp Ser Arg
                20                  25                  30
Met Tyr Thr Phe Ser Lys Lys Asn Ala Ile Asn Asp Leu Glu Glu Asp
            35                  40                  45
Pro Leu Ile Lys Ser Val Glu Ile His Lys Gln Leu Pro Asn Thr Leu
        50                  55                  60
Asn Val Asp Ile Thr Glu Asn Glu Ile Ile Ala Leu Val Lys Tyr Lys
65                  70                  75                  80
Gly Lys Tyr Leu Pro Leu Leu Glu Asn Gly Lys Leu Leu Lys Gly Ser
                85                  90                  95
Asn Asp Val Lys Ile Asn Asp Ala Pro Val Met Asp Gly Phe Lys Gly
            100                 105                 110
Thr Lys Glu Asp Asp Met Ile Lys Ala Leu Ser Glu Met Thr Pro Glu
        115                 120                 125
```

Val Arg Arg Tyr Ile Ala Glu Val Thr Tyr Ala Pro Ser Lys Asn Lys
            130                 135                 140

Gln Ser Arg Ile Glu Leu Phe Thr Thr Asp Gly Leu Gln Val Ile Gly
145                 150                 155                 160

Asp Ile Ser Thr Ile Ser Lys Lys Met Lys Tyr Tyr Pro Gln Met Ser
                165                 170                 175

Gln Ser Leu Ser Arg Asp Ser Ser Gly Lys Leu Lys Thr Arg Gly Tyr
            180                 185                 190

Ile Asp Leu Ser Val Gly Ala Ser Phe Ile Pro Tyr Arg Gly Asn Thr
        195                 200                 205

Ser Ser Gln Ser Glu Ser Asp Lys Asn Val Thr Lys Ser Ser Gln Glu
    210                 215                 220

Glu Asn Gln Ala Lys Glu Glu Leu Gln Ser Val Leu Asn Lys Ile Asn
225                 230                 235                 240

Lys Gln Ser Ser Lys Asn Asn
            245

<210> SEQ ID NO 23
<211> LENGTH: 75
<212> TYPE: PRT
<213> ORGANISM: Artificial Sequence
<220> FEATURE:
<223> OTHER INFORMATION: extramembranous DivIC sequence

<400> SEQUENCE: 23

Lys His Arg Asn Asp Ile Asp Ala Gln Glu Arg Lys Ala Lys Glu Ala
1               5                   10                  15

Gln Phe Gln Lys Gln Gln Asn Glu Glu Ile Ala Leu Lys Glu Lys Leu
            20                  25                  30

Asn Asn Leu Asn Asp Lys Asp Tyr Ile Glu Lys Ile Ala Arg Asp Asp
        35                  40                  45

Tyr Tyr Leu Ser Asn Lys Gly Glu Val Ile Phe Arg Leu Pro Glu Asp
    50                  55                  60

Lys Asp Ser Ser Ser Lys Ser Ser Lys Lys
65                  70                  75

<210> SEQ ID NO 24
<211> LENGTH: 68
<212> TYPE: PRT
<213> ORGANISM: Artificial Sequence
<220> FEATURE:
<223> OTHER INFORMATION: extramembranous FtsL sequence

<400> SEQUENCE: 24

Lys Met Asp Ala Tyr Asp Thr Arg Gly Lys Ile Ala Asp Leu Asp Tyr
1               5                   10                  15

Lys Ile Asp Lys Gln Ser Ser Glu Asn Ser Ala Leu Gln Ser Glu Ile
            20                  25                  30

Lys Lys Asn Ser Ser Tyr Glu Arg Ile Tyr Glu Lys Ala Lys Lys Gln
        35                  40                  45

Gly Met Ser Leu Glu Asn Asp Asn Val Lys Val Val Arg Ser Asn Gly
    50                  55                  60

Glu Ala Lys Asn
65

<210> SEQ ID NO 25
<211> LENGTH: 239
<212> TYPE: PRT

<213> ORGANISM: Artificial Sequence
<220> FEATURE:
<223> OTHER INFORMATION: T7-tag / intermediate bases / YdiE
      extramembranous / intermediate bases / His-tag sequence

<400> SEQUENCE: 25

Met Ala Val His His Ile Ala Gly His Ile Tyr Ala Asn His Ile Glu
1               5                   10                  15

Glu Pro Leu Thr Phe Pro Leu Ile Ala Leu Ile Val Ser Gly Gly His
                20                  25                  30

Thr Glu Leu Val Tyr Met Lys Asp His Leu Ser Phe Glu Val Ile Gly
            35                  40                  45

Glu Thr Arg Asp Asp Ala Val Gly Glu Ala Tyr Asp Lys Val Ala Arg
50                  55                  60

Thr Ile Gly Leu Asn Tyr Pro Gly Gly Pro Gln Val Asp Arg Leu Ala
65                  70                  75                  80

Ala Glu Gly Glu Asp Thr Tyr Ser Phe Pro Arg Val Trp Leu Asp Lys
                85                  90                  95

Asp Ser Tyr Asp Phe Ser Phe Ser Gly Leu Lys Ser Ala Val Ile Asn
                100                 105                 110

Gln Leu His Asn Gln Arg Gln Lys Asn Ile Pro Ile Ile Glu Ala Asn
            115                 120                 125

Val Ala Thr Ser Phe Gln Asn Ser Val Val Glu Val Leu Thr Phe Lys
130                 135                 140

Ala Ile Gln Ala Cys Lys Glu Tyr Gly Val Gln Arg Leu Ile Val Ala
145                 150                 155                 160

Gly Gly Val Ala Ser Asn Lys Gly Leu Arg Gln Ser Leu Ala Asp Gln
                165                 170                 175

Cys Lys Val Asn Asp Ile Gln Leu Thr Ile Pro Ser Pro Lys Leu Cys
                180                 185                 190

Thr Asp Asn Ala Ala Met Ile Gly Val Ala Gly His Tyr Leu Tyr Gln
            195                 200                 205

Gln Gly Arg Phe Ala Asp Leu Ala Leu Asn Gly His Ser Asn Ile Asp
        210                 215                 220

Leu Glu Glu Tyr Ser Ala Glu Leu Glu His His His His His His
225                 230                 235

<210> SEQ ID NO 26
<211> LENGTH: 257
<212> TYPE: PRT
<213> ORGANISM: Artificial Sequence
<220> FEATURE:
<223> OTHER INFORMATION: T7-tag / intermediate bases / DivIB
      extramembranous / intermediate bases / His-tag sequence; also
      termed DivB-2 in a preceding patent

<400> SEQUENCE: 26

Met Ala Pro Leu Ser Lys Ile Ala His Val Asn Ile Asn Gly Asn Asn
1               5                   10                  15

His Val Ser Thr Ser Lys Ile Asn Lys Val Leu Gly Val Lys Asn Asp
                20                  25                  30

Ser Arg Met Tyr Thr Phe Ser Lys Lys Asn Ala Ile Asn Asp Leu Glu
            35                  40                  45

Glu Asp Pro Leu Ile Lys Ser Val Glu Ile His Lys Gln Leu Pro Asn
        50                  55                  60

Thr Leu Asn Val Asp Ile Thr Glu Asn Glu Ile Ile Ala Leu Val Lys
65                  70                  75                  80

```
Tyr Lys Gly Lys Tyr Leu Pro Leu Leu Glu Asn Gly Lys Leu Leu Lys
                85                  90                  95

Gly Ser Asn Asp Val Lys Ile Asn Asp Ala Pro Val Met Asp Gly Phe
            100                 105                 110

Lys Gly Thr Lys Glu Asp Met Ile Lys Ala Leu Ser Glu Met Thr
        115                 120                 125

Pro Glu Val Arg Arg Tyr Ile Ala Glu Val Thr Tyr Ala Pro Ser Lys
    130                 135                 140

Asn Lys Gln Ser Arg Ile Glu Leu Phe Thr Thr Asp Gly Leu Gln Val
145                 150                 155                 160

Ile Gly Asp Ile Ser Thr Ile Ser Lys Lys Met Lys Tyr Tyr Pro Gln
                165                 170                 175

Met Ser Gln Ser Leu Ser Arg Asp Ser Ser Gly Lys Leu Lys Thr Arg
            180                 185                 190

Gly Tyr Ile Asp Leu Ser Val Gly Ala Ser Phe Ile Pro Tyr Arg Gly
        195                 200                 205

Asn Thr Ser Ser Gln Ser Glu Ser Asp Lys Asn Val Thr Lys Ser Ser
    210                 215                 220

Gln Glu Glu Asn Gln Ala Lys Glu Leu Gln Ser Val Leu Asn Lys
225                 230                 235                 240

Ile Asn Lys Gln Ser Ser Lys Asn Asn Leu Glu His His His His His
                245                 250                 255

His

<210> SEQ ID NO 27
<211> LENGTH: 85
<212> TYPE: PRT
<213> ORGANISM: Artificial Sequence
<220> FEATURE:
<223> OTHER INFORMATION: (T7-tag / intermediate bases / DivIC
      extramembranous / intermediate bases / His-tag sequence

<400> SEQUENCE: 27

Met Ala Lys His Arg Asn Asp Ile Asp Ala Gln Glu Arg Lys Ala Lys
1               5                   10                  15

Glu Ala Gln Phe Gln Lys Gln Asn Glu Glu Ile Ala Leu Lys Glu
            20                  25                  30

Lys Leu Asn Asn Leu Asn Asp Lys Asp Tyr Ile Glu Lys Ile Ala Arg
        35                  40                  45

Asp Asp Tyr Tyr Leu Ser Asn Lys Gly Glu Val Ile Phe Arg Leu Pro
    50                  55                  60

Glu Asp Lys Asp Ser Ser Ser Lys Ser Lys Lys Leu Glu His
65                  70                  75                  80

His His His His
            85

<210> SEQ ID NO 28
<211> LENGTH: 78
<212> TYPE: PRT
<213> ORGANISM: Artificial Sequence
<220> FEATURE:
<223> OTHER INFORMATION: T7-tag / intermediate bases / ftsL
      extramembranous / intermediate bases / His-tag sequence

<400> SEQUENCE: 28

Met Ala Lys Met Asp Ala Tyr Asp Thr Arg Gly Lys Ile Ala Asp Leu
1               5                   10                  15

Asp Tyr Lys Ile Asp Lys Gln Ser Ser Glu Asn Ser Ala Leu Gln Ser
```

```
                    20                  25                  30
Glu Ile Lys Lys Asn Ser Ser Tyr Glu Arg Ile Tyr Glu Lys Ala Lys
                35                  40                  45

Lys Gln Gly Met Ser Leu Glu Asn Asp Asn Val Lys Val Val Arg Ser
 50                  55                  60

Asn Gly Glu Ala Lys Asn Leu Glu His His His His His His
 65                  70                  75
```

```
<210> SEQ ID NO 29
<211> LENGTH: 33
<212> TYPE: DNA
<213> ORGANISM: Artificial Sequence
<220> FEATURE:
<223> OTHER INFORMATION: nucleotide primer

<400> SEQUENCE: 29
ataataccat ggctgttcat catattgcag gac                              33

<210> SEQ ID NO 30
<211> LENGTH: 36
<212> TYPE: DNA
<213> ORGANISM: Artificial Sequence
<220> FEATURE:
<223> OTHER INFORMATION: nucleotide primer

<400> SEQUENCE: 30
ataatactcg agttctgcag aatactcttc taaatc                           36

<210> SEQ ID NO 31
<211> LENGTH: 36
<212> TYPE: DNA
<213> ORGANISM: Artificial Sequence
<220> FEATURE:
<223> OTHER INFORMATION: nucleotide primer

<400> SEQUENCE: 31
ataataccat ggctccactt agtaaaattg cgcatg                           36

<210> SEQ ID NO 32
<211> LENGTH: 34
<212> TYPE: DNA
<213> ORGANISM: Artificial Sequence
<220> FEATURE:
<223> OTHER INFORMATION: nucleotide primer

<400> SEQUENCE: 32
ataatactcg agattattct tacttgattg tttg                             34

<210> SEQ ID NO 33
<211> LENGTH: 35
<212> TYPE: DNA
<213> ORGANISM: Artificial Sequence
<220> FEATURE:
<223> OTHER INFORMATION: nucleotide primer

<400> SEQUENCE: 33
ataataccat ggctaaacat cgcaatgata ttgat                            35

<210> SEQ ID NO 34
<211> LENGTH: 33
<212> TYPE: DNA
<213> ORGANISM: Artificial Sequence
<220> FEATURE:
<223> OTHER INFORMATION: nucleotide primer
```

```
<400> SEQUENCE: 34
ataattctcg agtttttcg aagattttga gct                             33

<210> SEQ ID NO 35
<211> LENGTH: 35
<212> TYPE: DNA
<213> ORGANISM: Artificial Sequence
<220> FEATURE:
<223> OTHER INFORMATION: nucleotide primer

<400> SEQUENCE: 35
ataataccat ggctaaaatg gatgcgtatg atacg                          35

<210> SEQ ID NO 36
<211> LENGTH: 33
<212> TYPE: DNA
<213> ORGANISM: Artificial Sequence
<220> FEATURE:
<223> OTHER INFORMATION: nucleotide primer

<400> SEQUENCE: 36
ataatactcg agatttttg cttcgccatt act                             33
```

COMBINATION VACCINE

REFERENCE TO RELATED APPLICFATIONS

This application is the US national phase entry of International Patent Application No. PCT/GB2012/050791, filed Apr. 11, 2012, which claims priority to GB Patent Application No. 1106162.9, filed Apr. 12, 2011.

FIELD OF THE INVENTION

The disclosure relates to a composition comprising two or more immunogenic staphylococcal polypeptides and a multivalent vaccine composition comprising the immunogenic staphylococcal polypeptides in the prevention or treatment of staphylococcal infections in humans and animals.

BACKGROUND

Vaccines protect against a wide variety of infectious diseases. Many modern vaccines are therefore made from protective antigens of the pathogen, which are isolated by molecular cloning and purified. These vaccines are known as 'subunit vaccines'. The development of subunit vaccines has been the focus of considerable research in recent years. The emergence of new pathogens and the growth of antibiotic resistance have created a need to develop new vaccines and to identify further candidate molecules useful in the development of subunit vaccines. Likewise the discovery of novel vaccine antigens from genomic and proteomic studies is enabling the development of new subunit vaccine candidates, particularly against bacterial pathogens. However, although subunit vaccines tend to avoid the side effects of killed or attenuated pathogen vaccines, their 'pure' status means that subunit vaccines do not always have adequate immunogenicity to confer protection.

An approach to improve the efficacy of vaccine compositions is to provide multivalent vaccines comprising dominant antigens that provoke both a B cell and T cell response thereby mounting a more rigorous immune response in the subject receiving the vaccine. A typical multivalent vaccine might be a whole cell vaccine comprising multiple antigenic molecules. For example the *Bacillus* Calmette Guerin ["BCG"] vaccine includes an attenuated *Mycobacterium bovis* strain that provokes protective immunity in humans. For many pathogens chemical or heat inactivation while it may give rise to vaccine immunogens that confer protective immunity also gives rise to side effects such as fever and injection site reactions. In the case of bacteria, inactivated organisms tend to be so toxic that side effects have limited the application of such crude vaccine immunogens and therefore vaccine development has lagged behind drug-development. Moreover, effective vaccine development using whole cell inactivated organisms suffers from problems of epitope masking, immunodominance, low antigen concentration and antigen redundancy.

Currently there is no effective vaccination procedure to prevent or treat *Staphylococcus aureus* infection. *S. aureus* is a bacterium whose normal habitat is the epithelial lining of the nose in about 20-40% of normal healthy people and is also commonly found on people's skin usually without causing harm. However, in certain circumstances, particularly when skin is damaged, this pathogen can cause infection. This is a particular problem in hospitals where patients may have surgical procedures and/or be taking immunosuppressive drugs. These patients are much more vulnerable to infection with *S. aureus* because of the treatment they have received. Antibiotic resistant strains of *S. aureus* have arisen since their wide spread use in controlling microbial infection. Methicillin resistant strains are prevalent and many of these resistant strains are also resistant to several other antibiotics.

*S. aureus* is therefore a major human pathogen capable of causing a wide range of diseases some of which are life threatening diseases including septicaemia, endocarditis, arthritis and toxic shock. This ability is determined by the versatility of the organism and its arsenal of components involved in virulence. At the onset of infection, and as it progresses, the needs and environment of the organism changes and this is mirrored by a corresponding alteration in the virulence determinants which *S. aureus* produces. At the beginning of infection it is important for the pathogen to adhere to host tissues and so a large repertoire of cell surface associated attachment proteins are made. The pathogen also has the ability to evade host defenses by the production of factors that reduce phagocytosis or interfere with the ability of the cells to be recognised by circulating antibodies.

There is therefore a continuing need to identify staphylococcal antigens that are protective and can be used in multivalent vaccines. The combinations may be used in combination with non-protein immunogenic molecules such as polysaccharide antigens and anti-bacterial agents to provide a treatment regimen for control of staphylococcal infection. It is also within the scope of this disclosure to modify the treatment regimen to immunize subjects with a series of temporally separated administrations as an alternative to the administration of a single vaccine comprising multiple antigens.

SUMMARY

This disclosure therefore relates to combination or multivalent immunogenic compositions and vaccines and their use in the prophylaxis and treatment of staphylococcal infections. We disclose polypeptides that individually are protective and are typically membrane spanning proteins that include an extracellular domain and are essential for staphylococcal cell growth. For example DivIB is an integral membrane protein comprising an intracellular domain, an intermembrane domain and an extracellular domain. DivIB and fragments thereof, provide protection from at least an *S. aureus* challenge in an animal model. The related gene DivIC is also an integral membrane protein the extracellular domain of which provokes protective immunity to staphylococcal infection. This disclosure also relates to antigens encoded by the genes PheP, YdiE and FtsL each of which have an extramembranous domain.

According to an aspect of the invention there is provided an immunogenic composition comprising two or more different polypeptides wherein said polypeptides are encoded by different staphylococcal genes selected from the group consisting of:

i) a polypeptide, or immunogenic fragment thereof, comprising or consisting of the amino acid sequence as represented in SEQ ID NO: 20;
  ii) a polypeptide, or immunogenic fragment thereof, comprising or consisting of the amino acid sequence as represented in SEQ ID NO: 21;
  iii) a polypeptide, or immunogenic fragment thereof, comprising or consisting of the amino acid sequence as represented in SEQ ID NO: 22;
  iv) a polypeptide, or immunogenic fragment thereof, comprising or consisting of the amino acid sequence as represented in SEQ ID NO: 23;

v) a polypeptide, or immunogenic fragment thereof, comprising or consisting of the amino acid sequence as represented in SEQ ID NO: 24; or vi) a modified staphylococcal polypeptide wherein said polypeptide is a staphylococcal polypeptide variant of the amino acid sequences presented in SEQ ID NO: 20, 21, 22, 23 or 24, wherein said sequences are modified by addition, deletion or substitution of one or more amino acid residues which modified polypeptides have retained or enhanced immunogenicity when compared to the polypeptide as represented in SEQ ID NO: 20, 21, 22, 23 or 24.

A modified staphylococcal polypeptide or variant staphylococcal polypeptide may differ in amino acid sequence by one or more substitutions, additions, deletions, truncations that may be present in any combination. Among preferred variants are those that vary from a reference polypeptide by conservative amino acid substitutions. Such substitutions are those that substitute a given amino acid by another amino acid of like characteristics. The following non-limiting list of amino acids are considered conservative replacements (similar): a) alanine, serine, and threonine; b) glutamic acid and aspartic acid; c) asparagine and glutamine d) arginine and lysine; e) isoleucine, leucine, methionine and valine and f) phenylalanine, tyrosine and tryptophan. Most highly preferred are variants that retain or enhance the immunogenicity and/or activity as the reference polypeptide from which it varies.

In one embodiment, the variant polypeptides have at least 80-89% sequence identity, more preferably at least 90% identity, even more preferably at least 95% identity, still more preferably at least 97% identity, and most preferably at least 99% identity with the full length amino acid sequences illustrated herein.

In a preferred embodiment of the invention said immunogenic composition comprises or consists essentially of 2, 3, 4 or 5 staphylococcal polypeptides.

In a preferred embodiment of the invention there is provided an immunogenic composition comprising:
  i) a polypeptide comprising SEQ ID NO: 20, or an antigenic fragment thereof; and
  ii) a polypeptide comprising SEQ ID NO: 21, or antigenic fragment thereof.

In a preferred embodiment of the invention there is provided an immunogenic composition comprising:
  i) a polypeptide comprising SEQ ID NO: 20, or an antigenic fragment thereof; and
  ii) a polypeptide comprising SEQ ID NO: 22, or an antigenic fragment thereof.

In a preferred embodiment of the invention there is provided an immunogenic composition comprising:
  i) a polypeptide comprising SEQ ID NO:20, or an antigenic fragment thereof; and
  ii) a polypeptide comprising SEQ ID N0.23, or an antigenic fragment thereof.

In a preferred embodiment of the invention there is provided a composition comprising:
  i) a polypeptide comprising SEQ ID NO: 20, or an antigenic fragment thereof; and
  ii) a polypeptide comprising SEQ ID NO: 24, or an antigenic fragment thereof.

In a preferred embodiment of the invention there is provided an immunogenic composition comprising:
  i) a polypeptide comprising SEQ ID NO: 20, or an antigenic fragment thereof; and
  ii) a polypeptide comprising SEQ ID NO: 23 and 24, or an antigenic fragment thereof.

In a preferred embodiment of the invention there is provided an immunogenic composition comprising:
  i) a polypeptide comprising SEQ ID NO: 20, or an antigenic fragment thereof; and
  ii) a polypeptide comprising SEQ ID NO: 21 and 22, or an antigenic fragment thereof.

In a preferred embodiment of the invention there is provided an immunogenic composition comprising:
  i) a polypeptide comprising SEQ ID NO: 20, or an antigenic fragment thereof; and
  ii) a polypeptide comprising SEQ ID NO: 22 and 23, or an antigenic fragment thereof.

In a preferred embodiment of the invention there is provided an immunogenic composition comprising:
  i) a polypeptide comprising SEQ ID NO: 20, or an antigenic fragment thereof; and
  ii) a polypeptide comprising SEQ ID NO: 21 and 23, or an antigenic fragment thereof.

In a preferred embodiment of the invention there is provided an immunogenic composition comprising:
  i) a polypeptide comprising SEQ ID NO: 20, or an antigenic fragment thereof; and
  ii) a polypeptide comprising SEQ ID NO: 22 and 24, or an antigenic fragment thereof.

In a preferred embodiment of the invention there is provided an immunogenic composition comprising:
  i) a polypeptide comprising SEQ ID NO: 20, or an antigenic fragment thereof; and
  ii) a polypeptide comprising SEQ ID NO: 21 and 24, or an antigenic fragment thereof.

In a preferred embodiment of the invention there is provided an immunogenic composition comprising:
  i) a polypeptide comprising SEQ ID NO: 20, or an antigenic fragment thereof; and
  ii) a polypeptide comprising SEQ ID NO: 21, 23 and 24, or an antigenic fragment thereof.

In a preferred embodiment of the invention there is provided an immunogenic composition comprising:
  i) a polypeptide comprising SEQ ID NO: 20, or an antigenic fragment thereof; and
  ii) a polypeptide comprising SEQ ID NO: 22, 23 and 24, or an antigenic fragment thereof.

In a preferred embodiment of the invention there is provided an immunogenic composition comprising:
  i) a polypeptide comprising SEQ ID NO: 20, or an antigenic fragment thereof; and
  ii) a polypeptide comprising SEQ ID NO: 21, 22 and 24, or an antigenic fragment thereof.

In a preferred embodiment of the invention there is provided an immunogenic composition comprising:
  i) a polypeptide comprising SEQ ID NO: 20, or an antigenic fragment thereof; and
  ii) a polypeptide comprising SEQ ID NO: 21, 22 and 23, or an antigenic fragment thereof.

In a preferred embodiment of the invention there is provided an immunogenic composition comprising:
  i) a polypeptide comprising SEQ ID NO: 20, or an antigenic fragment thereof; and
  ii) a polypeptide comprising SEQ ID NO: 21, 22, 23 and 24, or an antigenic fragment thereof.

In an alternative preferred embodiment of the invention there is provided an immunogenic composition comprising:
  i) a polypeptide comprising SEQ ID NO: 21, or an antigenic fragment thereof; and
  ii) a polypeptide comprising SEQ ID NO: 22, or an antigenic fragment thereof.

In a preferred embodiment of the invention there is provided an immunogenic composition comprising:
i) a polypeptide comprising SEQ ID NO: 21, or an antigenic fragment thereof; and
ii) a polypeptide comprising SEQ ID NO: 23, or an antigenic fragment thereof.

In a preferred embodiment of the invention there is provided an immunogenic composition comprising:
i) a polypeptide comprising SEQ ID NO: 21, or an antigenic fragment thereof; and
ii) a polypeptide comprising SEQ ID NO: 24, or an antigenic fragment thereof.

In a preferred embodiment of the invention there is provided an immunogenic composition comprising:
i) a polypeptide comprising SEQ ID NO: 21, or an antigenic fragment thereof; and
ii) a polypeptide comprising 23 and 24, or an antigenic fragment thereof.

In a preferred embodiment of the invention there is provided an immunogenic composition comprising:
i) a polypeptide comprising SEQ ID NO: 21, or an antigenic fragment thereof; and
ii) a polypeptide comprising SEQ ID NO: 22, and 23, or an antigenic fragment thereof.

In a preferred embodiment of the invention there is provided an immunogenic composition comprising:
i) a polypeptide comprising SEQ ID NO: 21, or an antigenic fragment thereof; and
ii) a polypeptide comprising SEQ ID NO: 22 and 24, or an antigenic fragment thereof.

In a preferred embodiment of the invention there is provided an immunogenic composition comprising:
i) a polypeptide comprising SEQ ID NO: 21, or an antigenic fragment thereof; and
ii) a polypeptide comprising SEQ ID NO: 22, 23 and 24, or an antigenic fragment thereof.

In an alternative preferred embodiment of the invention there is provided an immunogenic composition comprising:
i) a polypeptide comprising SEQ ID NO: 22, or an antigenic fragment thereof; and
ii) a polypeptide comprising SEQ ID NO: 23 and 24, or an antigenic fragment thereof.

In a preferred embodiment of the invention there is provided an immunogenic composition comprising:
i) a polypeptide comprising SEQ ID NO: 22, or an antigenic fragment thereof; and
ii) a polypeptide comprising SEQ ID NO: 23, or an antigenic fragment thereof.

In a preferred embodiment of the invention there is provided an immunogenic composition comprising:
i) a polypeptide comprising SEQ ID NO: 22, or an antigenic fragment thereof; and
ii) a polypeptide comprising SEQ ID NO: 24, or an antigenic fragment thereof.

In an alternative preferred embodiment of the invention there is provided an immunogenic composition comprising:
i) a polypeptide comprising SEQ ID NO: 23, or an antigenic fragment thereof; and
ii) a polypeptide comprising SEQ ID NO: 24, or an antigenic fragment thereof.

In a preferred embodiment of the invention said composition is a vaccine composition and includes at least one carrier and/or adjuvant.

DETAILED DESCRIPTION

Adjuvants (immune potentiators or immunomodulators) have been used for decades to improve the immune response to vaccine antigens. The incorporation of adjuvants into vaccine formulations is aimed at enhancing, accelerating and prolonging the specific immune response to vaccine antigens. Advantages of adjuvants include the enhancement of the immunogenicity of weaker antigens, the reduction of the antigen amount needed for a successful immunisation, the reduction of the frequency of booster immunisations needed and an improved immune response in elderly and immunocompromised vaccines. Selectively, adjuvants can also be employed to optimise a desired immune response, e.g. with respect to immunoglobulin classes and induction of cytotoxic or helper T lymphocyte responses. In addition, certain adjuvants can be used to promote antibody responses at mucosal surfaces. Aluminium hydroxide and aluminium or calcium phosphate has been used routinely in human vaccines.

Adjuvants can be classified according to their source, mechanism of action and physical or chemical properties. The most commonly described adjuvant classes are gel-type, microbial, oil-emulsion and emulsifier-based, particulate, synthetic and cytokines. More than one adjuvant may be present in the final vaccine product according to the invention. They may be combined together with a single antigen or all antigens present in the vaccine, or each adjuvant may be combined with one particular antigen. The origin and nature of the adjuvants currently being used or developed is highly diverse. For example, aluminium based adjuvants consist of simple inorganic compounds and PLG is a polymeric carbohydrate. MDP is derived from bacterial cell walls; saponins are of plant origin, squalene is derived from shark liver and recombinant endogenous immunomodulators are derived from recombinant bacterial, yeast or mammalian cells. There are several adjuvants licensed for veterinary vaccines, such as mineral oil emulsions that are too reactive for human use. Similarly, complete Freund's adjuvant, although being one of the most powerful adjuvants known, is not suitable for human use.

A carrier is an immunogenic molecule which, when bound to a second molecule augments immune responses to the latter. The term carrier is construed in the following manner. A carrier is an immunogenic molecule which, when bound to a second molecule augments immune responses to the latter. Some antigens are not intrinsically immunogenic yet may be capable of generating antibody responses when associated with a foreign protein molecule such as keyhole-limpet haemocyanin or tetanus toxoid. Such antigens contain B-cell epitopes but no T cell epitopes. The protein moiety of such a conjugate (the "carrier" protein) provides T-cell epitopes which stimulate helper T-cells that in turn stimulate antigen-specific B-cells to differentiate into plasma cells and produce antibody against the antigen.

The vaccine compositions of the invention can be administered by any conventional route, including injection, intranasal spray by inhalation of for example an aerosol or nasal drops. The administration may be, for example, intravenous, intraperitoneal, intramuscular, intracavity, subcutaneous, or intradermally. The vaccine compositions of the invention are administered in effective amounts. An "effective amount" is that amount of a vaccine composition that alone or together with further doses, produces the desired response. In the case of treating a particular bacterial disease the desired response is providing protection when challenged by an infective agent.

In a preferred embodiment of the invention said vaccine composition is adapted for administration as a nasal spray.

In a preferred embodiment of the invention said vaccine composition is provided in an inhaler and delivered as an aerosol.

The amounts of vaccine will depend, of course, on the individual patient parameters including age, physical condition, size and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used sufficient to provoke immunity; that is, the highest safe dose according to sound medical judgment. It will be understood by those of ordinary skill in the art, however, that a patient may insist upon a lower dose or tolerable dose for medical reasons, psychological reasons or for virtually any other reasons.

The doses of vaccine administered to a subject can be chosen in accordance with different parameters, in particular in accordance with the mode of administration used and the state of the subject. In the event that a response in a subject is insufficient at the initial doses applied, higher doses (or effectively higher doses by a different, more localized delivery route) may be employed to the extent that patient tolerance permits.

In general, doses of vaccine are formulated and administered in effective immunizing doses according to any standard procedure in the art. Other protocols for the administration of the vaccine compositions will be known to one of ordinary skill in the art, in which the dose amount, schedule of injections, sites of injections, mode of administration and the like vary from the foregoing. Administration of the vaccine compositions to mammals other than humans, (e.g. for testing purposes or veterinary therapeutic purposes), is carried out under substantially the same conditions as described above. A subject, as used herein, is a mammal, preferably a human, and including a non-human primate, cow, horse, pig, sheep or goat.

The ratio of antigens may be varied in pair wise fashion. The ratio of each antigen may be 1:1, 2:1, 3:1, 4:1, 5:1, 6:1, 7:1, 8:1, 9:1 or 10:1 to optimize the response of the subject to particular combinations of antigen. For example the ratio of DivIB and YdiE may be varied as described above.

In a preferred embodiment of the invention there is provided a vaccine composition according to the invention that includes at least one additional anti-bacterial agent.

In a preferred embodiment of the invention said agent is a second different vaccine and/or immunogenic agent (for example a bacterial polypeptide and/or polysaccharide antigen).

According to a further aspect of the invention there is provided a composition comprising a nucleic acid molecule [s] comprising or consisting of nucleotide sequences of two or more different staphylococcal genes and encoding immunogenic polypeptides selected from the group consisting of:
  i) a nucleic acid molecule comprising or consisting of the nucleotide sequence as represented in SEQ ID NO: 1 or 6;
  ii) a nucleic acid molecule comprising or consisting of the nucleotide sequence as represented in SEQ ID NO: 2 or 7;
  iii) a nucleic acid molecule comprising or consisting of the nucleotide sequence as represented in SEQ ID NO: 3 or 8;
  iv) a nucleic acid molecule comprising or consisting of the nucleotide sequence as represented in SEQ ID NO: 4 or 9;
  v) a nucleic acid molecule comprising or consisting of the nucleotide sequence as represented in SEQ ID NO: 5 or 10;
  vi) a nucleic acid molecule comprising or consisting of a nucleotide sequence wherein said sequence is degenerate as a result of the genetic code to the nucleotide sequence defined in i-v above; or
  vii) a nucleic acid molecule the complementary strand of which hybridizes under stringent hybridization conditions to the sequence in SEQ ID NO: 1, 2, 3, 4, 5, 6, 7, 8, 9 or 10 and wherein said nucleic acid molecule encodes a staphylococcal antigenic polypeptide.

Hybridization of a nucleic acid molecule occurs when two complementary nucleic acid molecules undergo an amount of hydrogen bonding to each other. The stringency of hybridization can vary according to the environmental conditions surrounding the nucleic acids, the nature of the hybridization method, and the composition and length of the nucleic acid molecules used. Calculations regarding hybridization conditions required for attaining particular degrees of stringency are discussed in Sambrook et al., Molecular Cloning: A Laboratory Manual (Cold Spring Harbor Laboratory Press, Cold Spring Harbor, N.Y., 2001); and Tijssen, Laboratory Techniques in Biochemistry and Molecular Biology-Hybridization with Nucleic Acid Probes Part I, Chapter 2 (Elsevier, New York, 1993). The $T_m$ is the temperature at which 50% of a given strand of a nucleic acid molecule is hybridized to its complementary strand. The following is an exemplary set of hybridization conditions and is not limiting:

Very High Stringency (Allows Sequences that Share at Least 90% Identity to Hybridize)
  Hybridization: 5×SSC at 65° C. for 16 hours
  Wash twice: 2×SSC at room temperature (RT) for 15 minutes each
  Wash twice: 0.5×SSC at 65° C. for 20 minutes each
High Stringency (Allows Sequences that Share at Least 80% Identity to Hybridize)
  Hybridization: 5×–6×SSC at 65° C.-70° C. for 16-20 hours
  Wash twice: 2×SSC at RT for 5-20 minutes each
  Wash twice: 1×SSC at 55° C.-70° C. for 30 minutes each
Low Stringency (Allows Sequences that Share at Least 50% Identity to Hybridize)
  Hybridization: 6×SSC at RT to 55° C. for 16-20 hours
  Wash at least twice: 2×–3×SSC at RT to 55° C. for 20-30 minutes each.

In a preferred embodiment of the invention said composition is a vaccine composition and includes and includes at least one carrier and/or adjuvant.

The nucleic acid or DNA combination vaccines comprise nucleic acid molecules that encode antigenic polypeptides as herein disclosed. The specific combinations of polypeptide antigens as represented by amino acid SEQ ID can be substituted for the corresponding nucleotide SEQ ID as herein disclosed in the manufacture of DNA vaccines.

According to a further aspect of the invention there is provided a combination vaccine according to the invention for use in the protection or treatment of a subject animal to a staphylococcal infection or condition that results from a staphylococcal infection.

In a preferred embodiment of the invention said staphylococcal infection is caused by a staphylococcal species selected from the group consisting of: *S. epidermidis, S. aureus, S. hominis, S. haemolyticus, S. warneri, S. capitis, S. saccharolyticus, S. auricularis, S. simulans, S. saprophytics, S. cohnii, S. xylosus, S. hyicus, S. caprae, S. gallinarum, S. intermedius,*

In a further preferred embodiment of the invention said staphylococcal species is *S. aureus* or *S. epidermidis*.

In a preferred embodiment of the invention said subject is a human.

In an alternative preferred embodiment of the invention said subject is a non-human animal, preferably a livestock animal, for example cattle.

In a preferred embodiment of the invention said live stock animal is vaccinated against bacterial mastitis caused by staphylococcal bacterial cells.

In a preferred embodiment of the invention said life stock animal is a caprine animal (e.g. sheep, goat).

In a preferred embodiment of the invention said life stock animal is a bovine animal (e.g. a cow).

Staphylococcal mastitis is a serious condition that affects live stock and can result in considerable expense with respect to controlling the disease through administration of antibiotics and in terms of lost milk yield. The vaccine according to the invention provides cost effective control of bacterial, in particular staphylococcal mastitis.

Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

An embodiment of the invention will now be described by example only and with reference to the following FIGURES Tables 3 and 4 illustrate the vaccination of a mouse model with a combination antigens of the extracellular domains of YdiE and DivIB compared to individual antigen vaccinations.
Materials and Methods
Construction of Plasmids for the Overexpression in *E. coli* of the Extramembranous Fragments of the *S. aureus* Proteins The PheP selected peptide was synthesized and conjugated through a cysteine at its C terminal to the carrier protein KLH to undertake as a chimeric protein used in vaccinations. The extramembranous fragments of YdiE, DivIB, DivIC and FtsL were PCR amplified from the chromosome of strain *S. aureus* SH1000 (Horsburgh M J, Aish J L, White I J, Shaw L, Lithgow J K, Foster S J: sigmaB modulates virulence determinant expression and stress resistance: characterization of a functional rsbU strain derived from *Staphylococcus aureus* 8325-4. *J Bacteriol* 2002, 184:5457-5467) using oligonucleotide pairs indicated on Table 1 according to the following PCR reaction conditions: 1 initial denaturation cycle of 94° C. for 4 min; 30 amplification cycles of denaturation 94° C. for 30 seconds, annealing 45° C. for 30 seconds, and extension at 72° C. for up to 2.5 minutes; finally, ongoing amplification rounds were allow to complete at 72° C. for 4 min.

The restrictions sites engineered within the oligonucleotides are also indicated in Table 1 (underlined; NcoI or XhoI). The amplified fragments were digested with the corresponding restriction enzymes (NcoI for the 5' end, and XhoI for the 3' end) and cloned into the equivalent sites of the pET-21d(+) expression vector from Novagen (Cat. No. 69743-3) and resulting in the overexpression plasmids indicated in Table 1 generating a T7-tagged (partial, at the N-terminal) and 6×His-tagged (at the C-terminal end) form of the extramembranous fragments. In the SEQ IDs the T7- and His-tags are indicated in bold, and the extramembranous portion of the proteins of interest are underlined. The over expression plasmids were transferred into *E. coli* BL21 for over expression of the recombinant protein fragment.

The cloning of the PCR amplified fragment indicated above into the recipient pET21d(+) recipient plasmid vector at the NcoI and XhoI sites entailed the addition of hinge amino acids between the T7-tag and the extramembranous fragment, and between the latter and the His-tag. These amino acids are neither bold nor underlined in the SEQ IDs.
Over Expression of SEQ ID NO: 25-28

SEQ ID NOs 25 through 28 were over expressed from plasmids pGL597, pGL601, pALB26, and pALB27 in *E. coli* BL21 strain using Brain Heart Infusion Broth (CM0225, Oxoid, United Kingdom) in the presence of 100 µg/ml ampicillin and the Plac promoter gratuitous inducer IPTG (Isopropyl β-D-1-thiogalactopyranoside, 1 mM) for 4 to 6 hours at 37° C. and vigorous shaking. Following harvesting of the cells by centrifugation (5,000×g for 15 minutes at 4° C.) and subsequent lysis with 1 mg/ml lysozyme in phosphate buffer (Buffer A; 0.1M pH7.2) containing 0.5M NaCl) for one hour and subsequent sonication (3 cycles of 10 second pulses in sonicating water bath) the soluble and insoluble forms of the proteins of interest were separated by centrifugation at 13,000×g for 10 minutes. The precipitate was then resuspended in Buffer A containing 8M urea by freeze/thawing (3 cycles of freezing at −80° C. for 10 minutes and subsequent thawing to room temperature) and sonication (3 cycles of 10 second pulses in sonicating water bath), and subsequent centrifugation for 25 minutes at 18,000×g). The over expressed proteins of interest in the supernatant and the solubilised pellet were purified by initial specific binding (through their His-tag) to a nickel (NiSO4)-bound Sepharose chromatography column (Ni-Sepharose) and elution with an imidazole solution run through the column in the following stepwise manner: 5% for 5 minutes, 30% for 60 minutes, 35% for 60 minutes, 50% for 100 minutes and 55% for 100 minutes. Fractions from this stepwise elution were analysed in acrylamide denaturing gels with a 4% acrylamide/bis-acrilamide stacking layer and a 12% acrylamide/bis-acrylamide separating layer. The fractions containing the over expressed proteins of interest were pooled and dyalized against sterile phosphate buffer (8 g NaCl, 0.2 g KCl, 1.44 g $Na_2HPO_4$, 0.24 g $KH_2PO_4$, per liter of distilled $H_2O$, pH 7.4).

All the proteins of interest were successfully over expressed from the indicated strains and under the indicated conditions. They were also subsequently extracted from the total cellular protein content of the over expressing *E. coli* strains with more than 95% purity. Examples of the purification obtained for each of the proteins are indicated below.
Evaluation of Vaccination-Mediated Protection of Balb/C Mice Against Infection by *S. aureus*

One week after the second boost each animal was infected with an i.v. (tail vein) injection of 100 microliters of endotoxin-free PBS containing $1.1 \times 10^7$ ($\pm 0.5 \times 10^7$) cells of *S. aureus* strain Newman. The latter were prepared from cultures growing to early stationary phase in Brain Heart Infusion medium (BHI), which were then washed three times with the same volume of PBS.

After 10 to 14 days the animals were sacrificed according to Schedule 1 cervical dislocation. The pair of kidneys from each animal was extracted in aseptic conditions, and homogenized in sterile PBS. Serial dilutions of the kidney homogenates were carried out in PBS and plated on BHI agar plates. Plates containing between 10 to 150 staphylococcal colonies were counted and dilution corrected. The number of viable cells in the kidneys was inferred from the number of colony forming units (CFU) on the plates. Evaluation of the possible protection against infection conferred by vaccination with DivIB-2 was determined from difference in the number of S. aureus cells in the kidneys of animals vaccinated with KLH and those vaccinated with DivIB-2. The statistic significance of the difference was calculated using the Mann-Whitney test. A significantly higher (p<0.05) number of S. aureus in KLH vaccinated animals compared to the DivIB-2 vaccinated animals was concluded as protection.

Vaccination: Generic Protocol for Polyvalent Vaccines

Combination (or polyvalent) vaccines including variations of the antigens (conjugated selected PheP peptide, YdiE, DivIB, DivIC and FtsL) will follow an identical protocol with the following modifications. The vaccine priming and boost mixtures will contain rather than a single component 2 or more of the components. The total volume of mixed vaccine used for priming and boosting injections will fluctuate in a range of 50-100 microliters per animal. Similarly the total amount in each of those injections may vary between 50-100 micrograms. The amount of each antigen to contribute to the total amount of vaccine in the priming or boosting mix will vary between 20% to 80% of the total.

The various combinations of antigens to be evaluated as a vaccine mix will be undertaken according to the matrix in Table 2. The combinations are grouped in 3 tiers. Depending on results from the $1^{st}$ Tier of experiments the $2^{nd}$ Tier of experiments would be undertaken accordingly, and depending on the results from the latter the $3^{rd}$ Tier will be undertaken. In each Tier a vaccination experiment will contain an antigen in the Y axis, together with those ticked along the X axis, and labelled with the same colour. Each vaccination experiment is labelled with a different colour.

EXAMPLE 1

The experimental sample consisted in a combination antigen of the extracellular domains of YdiE and DivIB. The amount of antigen administered to each mouse (Female Balb/C, approx. 5-6 weeks old) was 5 ug of YdiE plus 50 ug of DivIB. Those amounts were contained within 100 ul of eluent consisting on a 50:50 v:v of PBS (Phosphate Buffer Saline) and Complete Freund's Adjuvant (used for the vaccination priming) or Incomplete Freund's Adjuvant (used for the vaccination boost). Priming was undertaken day 0, Boost 1 at 14 days, and Boost 2 at 21 days. Subsequently, 7 days later, i.e., at day 28 the animals were infected with Staphylococcus aureus strain Newman. Each test group (control and experimental) had 10 animals. The bacterial dose administered to the animals (both, control and experimental) contained $4 \times 10^6$ bacteria in 100 ul of PBS. The infection period was run for 3 days, and the weight of the animals was monitored daily (we also extracted organs to evaluate bacterial loads in organs, Table 4). At that point the animals were sacrificed. The output of the experiment was calculated as the percentage body weight loss between day 3 and day 0 for every animal. The results of these experiments are shown in Table 3. Statistical analysis of data in Table 3: TEST: Non-parametric statistical hypothesis test—Mann-Whitney U SELECTED OPTIONS: Two-tailed, unpaired, 95% confidence interval.
RESULTS: (two group comparison)
II and I: p=0.622
III and I: p=0.039*
IV and I: p=0.001*
II and III: p=0.061
II and IV: p=0.008*
III and IV: p=0.158
   *comparisons with statistically significant difference between the groups Statistical analysis Table 4:
TEST: Non-parametric statistical hypothesis test—Mann-Whitney U
SELECTED OPTIONS: Two-tailed, unpaired, 95% confidence interval.
RESULTS: (two group comparison)
II and I: p=0.2
III and I: p=0.105
IV and I: p=0.009*
II and III: p=0.378
II and IV: p=0.131
III and IV: p=0.504
   *comparisons with statistically significant difference between the groups

TABLE 1

Oligonucleotide sequences

| Progenitor gene name | Code - complete gene progenitor sequence | Code - fragment sequence amplified from progenitor | Oligonucleotide name | Oligonucleotide sequence code | Oligonucleotide sequence | Name of the resulting over-expression plasmids |
|---|---|---|---|---|---|---|
| ydiE/gcp | Sequence 2 | Sequence 21 | 5'GLUSh318B | Sequence 29 | ATAATA<u>CCATGG</u>CTGTTCATCATATTGCAGGAC | pGL597 |
|  |  |  | 3'GLUSh318B | Sequence 30 | ATAATA<u>CTCGAG</u>TTCTGCAGAATACTCTTCTAAATC |  |
| divIB | Sequence 3 | Sequence 22 | 5'GLUSh341C | Sequence 31 | ATAATA<u>CCATGG</u>CTCCACTTAGTAAAATTGCGCATG | pGL601 |
|  |  |  | 3'GLUSh341C | Sequence 32 | ATAATA<u>CTCGAG</u>ATTATTCTTACTTGATTGTTTG |  |
| divIC | Sequence 4 | Sequence 23 | ALB21 | Sequence 33 | ATAATA<u>CCATGG</u>CTAAACATCGCAATGATATTGAT | pALB26 |
|  |  |  | ALB22 | Sequence 34 | ATAATT<u>CTCGAG</u>TTTTTTCGAAGATTTTGAGCT |  |
| ftsL | Sequence 5 | Sequence 24 | ALB19 | Sequence 35 | ATAATA<u>CCATGG</u>CTAAAATGGATGCGTATGATACG | pALB27 |
|  |  |  | ALB20 | Sequence 36 | ATAATA<u>CTCGAG</u>ATTTTTTGCTTCGCCATTACT |  |

CCATGG: NcoI
CTCGAG: XhoI

TABLE 2

Multivalent vaccine experiments: Vaccine combinations

| | Antigen | | | | | | | | | | | |
|---|---|---|---|---|---|---|---|---|---|---|---|---|
| | Tier 1 | | | | Tier 2 | | | | Tier 3 | | | |
| | YdiE | DivIB | DivIC | FtsL SEQ 5 SEQ 10 SEQ 19 SEQ 24 | YdiE | DivIB | DivIC | FtsL | YdiE | DivIB | DivIC | FtsL |
| PheP | ✓ | ✓ | ✓ | ✓ | | | | | | | | |
| SEQ 1 | ✓ | ✓ | | | | | | | | | | |
| SEQ 6 | | | | | | | ✓ | ✓ | | | | |
| SEQ 15 | | | | | | | | | ✓ | | | |
| SEQ 20 | | | | | | | | | | | | |
| | | | | | | | | | | | ✓ | |
| | | | | | | | | | | | | ✓ |
| YdiE | | ✓ | | | | | | | | | | |
| SEQ 2 | | | | | | ✓ | ✓ | ✓ | | | | |
| SEQ 7 | | | | | | ✓ | ✓ | | | | | |
| SEQ 16 | | | | | | | | | | | ✓ | |
| SEQ 21 | | | | | | | | | | | | ✓ |
| DivIB | | | ✓ | ✓ | | | | | | | | |
| SEQ 3 | | | | | | | ✓ | | | | | |
| SEQ 8 | | | | | | | | ✓ | | | | |
| SEQ 17 | | | | | | | | | | | | |
| SEQ 22 | | | | | | | | | | | | |
| DivIC | | | | | | | | ✓ | | | | |
| SEQ 4 | | | | | | | | | | | | |
| SEQ 9 | | | | | | | | | | | | |
| SEQ 18 | | | | | | | | | | | | |
| SEQ 23 | | | | | | | | | | | | |

TABLE 3

% Body Weight Loss

| | Control Sample | Experimental Samples | | |
|---|---|---|---|---|
| Animal Number | I Adjuvant alone (Freunds) | II Antigen: rYdiE | III Antigen: rDivIB | IV Combination Antigen: rYdiE rDivIB |
| 1 | 11.1 | 11.3 | 13.1 | 2.3 |
| 2 | 12.7 | 4.3 | 0.0 | 2.0 |
| 3 | 9.7 | 9.0 | 3.5 | 0.0 |
| 4 | 7.6 | 12.6 | 0.5 | −4.3 |
| 5 | 9.4 | 1.0 | 7.1 | −0.5 |
| 6 | 9.9 | 6.2 | 3.3 | 1.8 |
| 7 | 2.0 | 3.8 | 2.1 | 1.5 |
| 8 | 4.2 | 5.3 | 1.9 | 1.4 |
| 9 | 1.0 | 3.4 | 1.0 | 1.6 |
| 10 | 3.1 | 7.0 | 6.8 | 3.9 |
| 11 | 7.7 | 4.7 | −2.5 | −0.5 |

TABLE 4

Log10 CFUs in Kidneys per animal

| | Control Sample | Experimental Samples | | |
|---|---|---|---|---|
| Animal Number | I Adjuvant alone (Freunds) | II Antigen: rYdiE | III Antigen: rDivIB | IV Combination Antigen: rYdiE rDivIB |
| 1 | 7.82 | 6.98 | 5.6 | 6.04 |
| 2 | 7.73 | 6.5 | 6.5 | 6.12 |
| 3 | 7.7 | 5.61 | 4.64 | 5.97 |
| 4 | 6.98 | 7.61 | 5.99 | 5.61 |
| 5 | 6.74 | 5.09 | 6.54 | 5.38 |
| 6 | 7.32 | 6.38 | 6.03 | 5.88 |
| 7 | 6.5 | 6.6 | 6.41 | 6.74 |
| 8 | 6.2 | 6.75 | 6.66 | 5.96 |
| 9 | 5.61 | 6.72 | 7.88 | 6.98 |
| 10 | 6.06 | 6.63 | 6.63 | 6.68 |
| 11 | 7.04 | 6.45 | | 4.74 |

The invention claimed is:

1. An immunogenic composition comprising two or more different isolated polypeptides wherein said immunogenic composition comprises:
   i) a polypeptide consisting of the amino acid sequence as represented in SEQ ID NO: 21; and
   ii) a polypeptide consisting of the amino acid sequence as represented in SEQ ID NO: 22.

2. The immunogenic composition according to claim 1, further comprising: a polypeptide comprising SEQ ID NO: 23.

3. The immunogenic composition according to claim 1, further comprising: a polypeptide comprising SEQ ID NO: 24.

4. The immunogenic composition according to claim 1, further comprising:
   i) a polypeptide comprising SEQ ID NO: 23; and
   ii) a polypeptide comprising SEQ ID NO: 24.

5. The immunogenic composition according to claim 1 further comprising at least one carrier and/or adjuvant.

6. The immunogenic composition according to claim 1, wherein said composition is adapted for administration as a nasal spray.

7. The immunogenic composition according to claim 1 wherein the composition is provided in an inhaler and delivered as an aerosol.

8. The immunogenic composition according to claim 1 wherein the composition includes at least one additional antibacterial agent.

9. A method for treating a *Staphylococcus aureus* infection in an animal subject, comprising administering an effective amount of an immunogenic composition according to claim 1.

10. The immunogenic composition of claim 5, wherein the adjuvant is selected from the group consisting of: aluminum hydroxide; aluminum phosphate; and calcium phosphate.

11. The immunogenic composition of claim 5, wherein said adjuvant is aluminum phosphate.

12. The composition of claim 11, wherein the adjuvant is formulated as a gel-type.

* * * * *